United States Patent [19]

Covington et al.

[11] Patent Number: 4,514,276
[45] Date of Patent: Apr. 30, 1985

[54] MICROELECTRONIC SENSOR ASSEMBLY

[75] Inventors: Arthur K. Covington, Newcastle Upon Tyne; Alastair Sibbald, Whitley Bay, both of England

[73] Assignee: Corning Glass Works, Corning, N.Y.

[21] Appl. No.: 366,710

[22] Filed: Apr. 8, 1982

[30] Foreign Application Priority Data

Oct. 31, 1981 [GB] United Kingdom ............... 8132895

[51] Int. Cl.³ ............................................. G01N 27/46
[52] U.S. Cl. .................................... 204/415; 204/400; 204/403; 330/307; 357/72; 357/80
[58] Field of Search ............... 204/400, 406, 415, 416, 204/418–420, 403, 1 P; 330/65, 307; 357/72, 74, 80

[56] References Cited

U.S. PATENT DOCUMENTS

| 3,088,905 | 5/1963 | Glover | 204/415 |
| 3,323,022 | 5/1967 | DaCosta | 357/80 |
| 3,380,905 | 4/1968 | Clark | 204/415 |
| 3,719,575 | 3/1973 | Niedrach et al. | 204/415 |
| 3,781,613 | 12/1973 | Robinson | 357/80 |
| 3,809,928 | 5/1974 | Evans | 330/307 |
| 3,830,719 | 8/1974 | Cavil | 204/196 |
| 3,933,612 | 1/1976 | Fischer et al. | 204/420 |
| 3,999,284 | 12/1976 | Bicher | 204/415 |
| 4,020,830 | 5/1977 | Johnson et al. | 204/412 |
| 4,062,750 | 12/1977 | Butler | 204/403 |
| 4,080,512 | 3/1978 | Ramet et al. | 357/80 |
| 4,133,732 | 1/1979 | Boeke | 204/419 |
| 4,133,735 | 1/1979 | Afromowitz et al. | 204/406 |
| 4,203,792 | 5/1980 | Thompson | 357/80 |
| 4,247,826 | 1/1981 | Gappa et al. | 330/307 |
| 4,273,636 | 6/1981 | Shimada et al. | 204/415 |
| 4,280,505 | 7/1981 | Dali et al. | 204/415 |
| 4,305,802 | 12/1981 | Koshiishi | 204/420 |

Primary Examiner—T. Tung
Attorney, Agent, or Firm—W. S. Zebrowski

[57] ABSTRACT

A microelectronic semiconductor element 12 is mounted on to a header 13, and integrally combined with one or more metallic sensing electrodes 20, 21 by encapsulation in a chemically and electrically inert material 19, to provide a miniature sensor assembly suitable for the detection and measurement of oxygen and other substances.

Gold or gold alloy semiconductor-device bonding wires are suitable as the metallic sensing electrodes and permit low-cost, mass-production capability. The basic assembly can be engineered in various forms for different biomedical applications and is readily modified, by the addition of appropriate electro-active films to the device surface, into a sensor for a variety of chemical and biochemical substances, including enzyme substrates.

5 Claims, 14 Drawing Figures

MICROELECTRONIC SENSOR ASSEMBLY

FIELD OF THE INVENTION

The present invention relates to an active, miniature, solid-state amperometric electrode assembly. In particular, the invention relates to a novel electrode assembly with integral microelectronic signal-processing, which is particularly well suited for application as an oxygen-sensing electrode.

DESCRIPTION OF THE PRIOR ART

Amperometric electrodes are well known and widely used for the detection and measurement of various chemical properties. ("Chemical properties", as used herein, shall be understood to include ion activity and concentration, presence and concentration of enzymes, substrates, antibodies, antigens, hormones and reducible gases, and the presence, concentration and activity of any of a variety of chemical and biochemical substances including the constituents of enzymatic systems, e.g. serum enzymes, glucose, lactates, pyruvates, creatinine, urea and the constituents of the immunochemical system).

The most widely used amperometric electrode is that used for measuring the partial pressure of oxygen ($pO_2$) in aqueous solution, commonly called a $pO_2$ electrode as originally developed by Clark (Trans. Am. Soc. Art. Int. Organs, 2 (1956), 41–8) which is based on amperometric measurement of oxygen reduced at a cathode maintained at typically −0.6 V with respect to, for example, a silver/silver-chloride (Ag/AgCl) non-polarised anode. The electrode is usually separated from the sample by an oxygen permeable membrane. (See "The acid-base status of the blood", (4th Ed.) (1974), pp. 175–181, O. Siggaard-Anderson, Alden and Mowbray Ltd., Oxford.) The cathode material must be relatively inert, and the surface area exposed to the sample must be small in order to restrict depletion of oxygen in the sample by the use of the electrode. In practice, this is usually achieved by sealing a fine platinum wire into a glass rod; for example the Radiometer (Copenhagen, Denmark) Type E5046 $pO_2$ electrode uses a 20 $\mu$m diameter platinum wire supported in a glass rod approximately 7 mm diameter and 12 mm in length. Cathodic reduction of oxygen by this electrode generates an output current of approximately 20 pA/mmHg $pO_2$ at 37° C., equivalent to a signal current of approximately 3 nA at normal atmospheric $pO_2$ at a polarizing voltage of −0.65 V. Thus, the source impedance of the electrode is $> 10^8$ ohms, and requires sophisticated and sensitive electronic instrumentation to perform current-to-voltage conversion and high-to-low impedance conversion in order to drive recording or display devices. The high electrode impedance requires that the cable between the electrode and the instrumentation must be carefully electrically screened with high quality, low-leakage cable and connectors, which add significantly to the bulk of the electrode. Conventional electrodes of this type are labour-intensive, and costly, to manufacture.

SUMMARY OF THE INVENTION

The present invention is concerned with the integration of the cathode electrode, or anode-cathode pair, and an appropriate microelectronic signal-processing device into a single unit, an integrated-circuit amperometric sensor (hereinafter referred to as I.C.A.S.) with unique and significant advantages over the present state-of-the-art electrode, especially with regard to biomedical usage. The present invention also describes techniques and materials for the fabrication of such electrodes which are entirely compatible with the present state-of-the-art of integrated circuit packaging.

The invention provides a miniature sensor assembly for the detection and electrochemical measurement of oxygen and/or other chemical properties of the environment to which it is exposed, comprising: a microelectronic semiconductor element (12) or plurality thereof; a metallic sensing electrode (20, 21) or plurality thereof; a substrate (13) for the physical support of the aformentioned and permitting external electrical connections to be made to the said semiconductor element(s) and electrode(s), integrally combined and enclosed, or partially enclosed, in a chemically-resistant electrically inert material (19) in such a way as to expose a portion of one or more of the metallic electrodes to the environment.

Furthermore, the basic conventional amperometric electrode forms the basis of other types of sensor, such as enzymatic-sensitive devices ("Multi-purpose electrode with different enzyme systems bound to collagen films", Bertrand, C., Coulet, P. R. and Gautheron, D. C., Anal. Chim. Acta (1981), 126, 23–34.); such devices are an important part of the present invention.

There are various ways in which our invention may be physically engineered; we do not exclude any such ways from the scope of the present invention. Two techniques are described hereinafter to illustrate different methods of fabrication of I.C.A.S. devices, which provide the most useful functional forms of sensor. The first technique provides sensors which are of similar physical dimensions to their conventional electrode counterparts, and may therefore be used as a direct and superior replacement for the latter, whereas the second technique describes the fabrication of I.C.A.S. devices of such dimensions, and in such a way, that they may be conveniently mounted as catheter-tip devices for in-vivo biomedical application, for example, as foetal scalp $pO_2$ electrodes.

The nature of the I.C.A.S. devices described herein also permits improvements in other areas of measurement, such as the transcutaneous $pO_2$ technique (see "Use of transcutaneous oxygen electrodes in intensive therapy", Aldaidy, W., Skeates, S. J., Hill, D. W., Tinker, J., Intensive Care Medicine (1977), 3 (1), 35–9.), which is presently limited by the relatively large surface area of the conventional electrodes employed therein.

The multifold advantages of the present invention over conventional state-of-the-art electrode systems are summarised below:

(1) The small size of I.C.A.S. devices is particularly useful for biomedical applications such as catheter-tip $pO_2$ sensors and for transcutaneous $pO_2$ measurements.

(2) Low-cost fabrication is easily achieved as the materials and techniques used are already widely used in integrated-circuit encapsulation procedures and are inexpensive.

(3) I.C.A.S. devices are inherently robust as they are solid-state transducers with no fragile components (e.g. glass) used in their construction.

(4) Mass-production is readily achieved as the fabrication techniques are well-suited to automation; minimal manual involvement is required.

(5) Multi-function integration is possible; a plurality of I.C.A.S. devices may be incorporated into a single assembly for the simultaneous detection and measurement of more than one chemical property.

(6) I.C.A.S. devices have low output impedances, typically 60 ohms (as opposed to approximately $2 \times 10^8$ ohms) due to the integrated current-to-voltage and impedance conversion circuitry. This eliminates the requirement for low-leakage screened cable access to the sensor, and is particularly important in foetal scalp $pO_2$ measurements where the environment contains substantial electrical interference and where physical placement of the sensor is difficult.

(7) Various ways of engineering I.C.A.S. devices provide sensors physically suited to widely different applications, as described hereinbefore.

(8) The electrical output and power requirements of the present invention are compatible with instrumentation which is presently used with conventional amperometric electrodes.

(9) The sensitivity of I.C.A.S. devices is superior to that of conventional amperometric systems which is limited by three factors: (i) the quality of the electrode surfaces; (ii) the quality of the electronic instrumentation: (iii) the quality of the electrical connections between the two former items (with regard to electrical leakage and adequacy of screening). I.C.A.S. devices eliminate the latter requirement.

In accordance with one aspect of the present invention, the I.C.A.S. device is engineered in such a way that it is dimensionally similar to its conventional counterpart, and therefore physically compatible with instrumentation already widely established in many analytical laboratories.

In accordance with another aspect of the present invention, the I.C.A.S. device is engineered to form sensors of such a small size and robust nature that they may be mounted on to catheter-tips or adapted to in-vivo biomedical application.

DESCRIPTION OF THE DRAWINGS

The objects and additional features of the present invention will become apparent from the following description taken in conjunction with preferred embodiments with reference to the accompanying drawings, in which.

Figure 1:
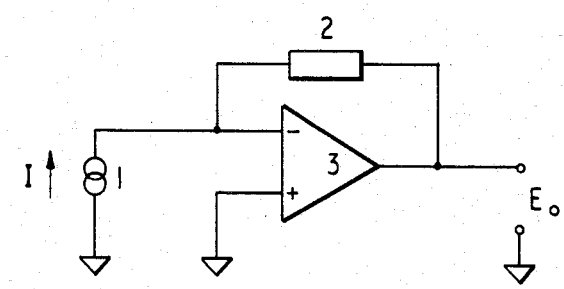
FIG. 1. shows a schematic diagram of an operational amplifier in current-to-voltage conversion configuration.
Figure 2:
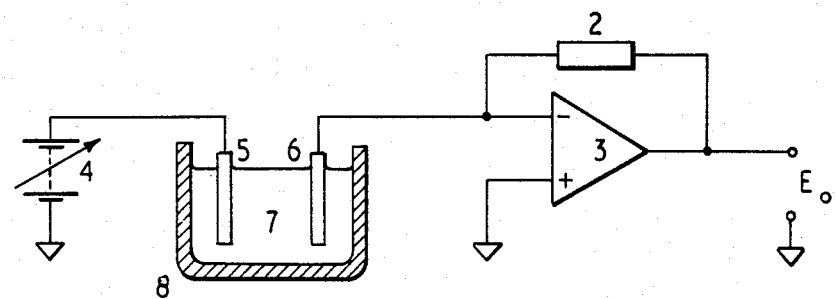
FIG. 2. shows an amperometric electrode pair, polarizing voltage source, and current-to-voltage converting amplifier (supra).

(For the purposes of clarity, the power supply connections to the amplifiers in FIGS. 1 and 2 have been omitted.)

DETAILED DESCRIPTION OF THE INVENTION

According to the present invention there is provided an amperometric electrode pair and associated semiconductor signal-processing element, or plurality thereof, integrated into a single assembly, and methods for the fabrication of the same using novel techniques. One or more of the amperometric sensing electrodes may be formed using silver, platinum or other noble metal in wire or strip form; however our technique employs the use of microelectronic bonding wires, such as those commonly used to make electrical connections between the microelectronic signal-processing element and the electrical connections by which external electrical access to it is gained (i.e. the bonding post of a microelectronic mount, such as a TO-5 type header), as one or more of the active sensing electrodes. This is feasible and highly desirable for three reasons:

(1) bonding wires are commonly made of gold (Au-1% Si);

(2) bonding wires are commonly 25 $\mu$m diameter;

(3) the sensing electrode can be bonded directly on to the microelectronic signal-processing element (or indirectly, via a bonding post).

There are various ways in which the appropriate current-to-voltage and impedance conversion may be effected using, for example, a dual-differential transistor pair or an operational amplifier, as will readily be appreciated by those skilled in the art. The technique and circuit elements described hereinafter are chosen as illustrative examples only and not intended to define or impose limitations on the way in which signal-processing is carried out. Rapid progress in microelectronic technology will undoubtedly generate more sophisticated semiconductor elements suitable for this application, and we do not exclude any of these from the scope of the present invention. For descriptive purposes we have chosen to illustrate the principle of operation and mode of fabrication of I.C.A.S. devices employing an operational amplifier (3) in current-to-voltage conversion mode (FIG. 1) as the signal-processing element, as will be readily appreciated by those skilled in the art, such that the input current I (from current source 1), feedback resistor R (2) and output voltage $E_o$ exhibit the relationship $-E_o = I \times R$. However, the currents generated by amperometric sensing electrodes are small, typically several nanoamperes for $pO_2 = 150$ mmHg, which necessitates the use of an amplifier with a high input impedance. Typically the CA 3140 (R.C.A. Ltd., New Jersey, U.S.A.) may be used for this purpose. For practical reasons, the use of a 10 megohm feedback resistor (2) provides an output $E_o$, of 10 mV per 1 nA input current, but this value may be varied in order to increase or reduce sensitivity.

FIG. 2 shows a conventional amperometric electrode pair connected to such circuitry as is described above, and a silver/silver-chloride anode 5, and an inert metallic (gold) cathode 6 exposed to a conducting aqueous solution 7 in a container 8, polarized by a variable voltage source 4, set to $\simeq +0.65$ v with respect to system common and hence with respect to the cathode which is connected to the amplifier virtual earth port. The current generated by the reduction of oxygen at the cathode 6 provides a proportional output voltage $E_o$ at low impedance (60 ohms) suitable for driving peripheral recording and/or display instrumentation.

Figure 3:
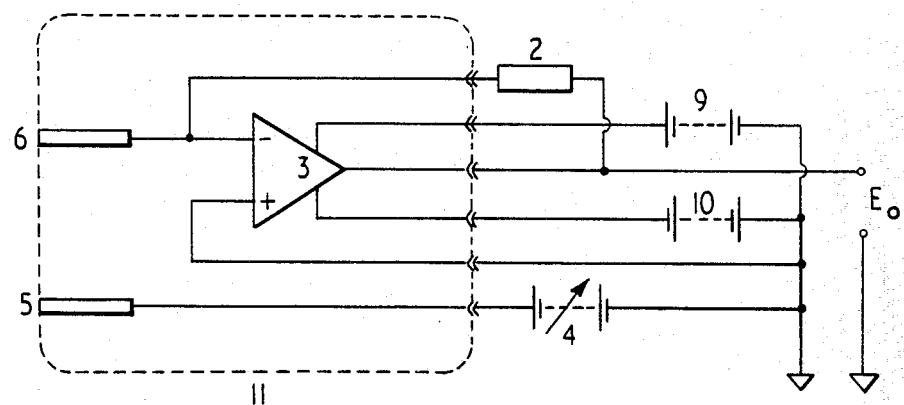
FIG. 3. shows an I.C.A.S. device in schematic form, together with associated circuitry.

The present invention (FIG. 3) comprises an assembly with sensing electrodes (5,6) and signal-processing element (3) integrated and encapulated into a single element (11), with electrical access to a polarizing voltage source (4), a power supply (9,10) and a gain-determining resistor (2). The physical implementation of such a device is described below; first, in TO-5 format; second, in "catheter-tip" format.

Figure 4:
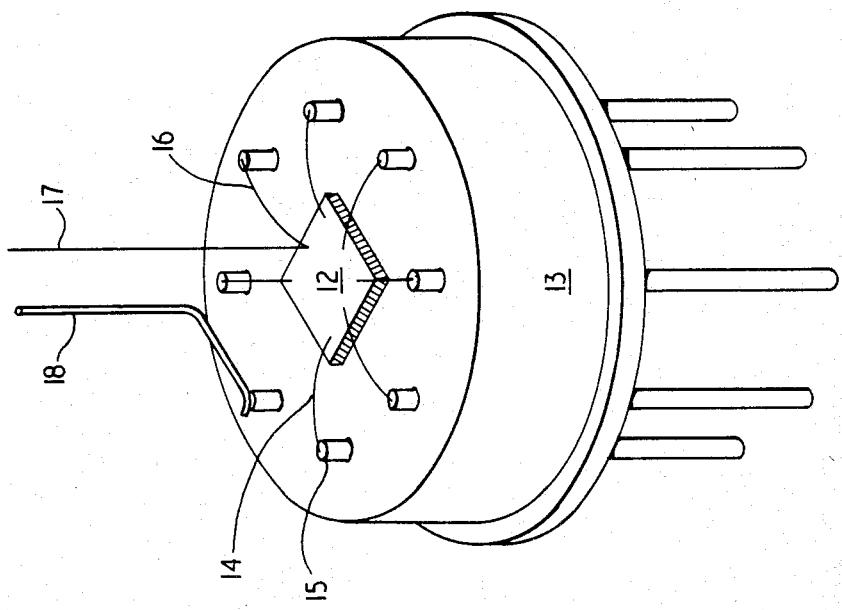
FIG. 4. shows a partially-completed I.C.A.S. device engineered on a conventional TO-5 type microelectronic header.
Figure 6:
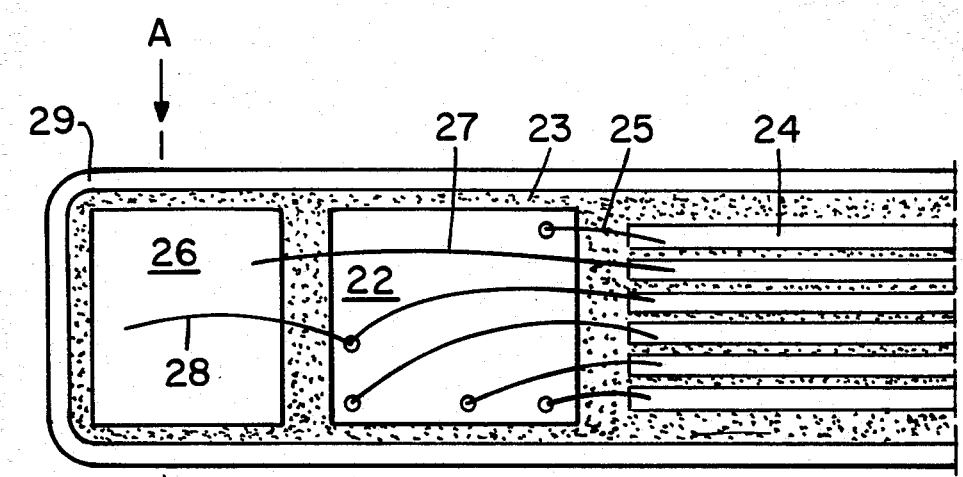
FIG. 6. shows the plan view of a partially-completed I.C.A.S. device mounted on a flexible printed circuit substrate for catheter-tip type operation.
Figure 7:
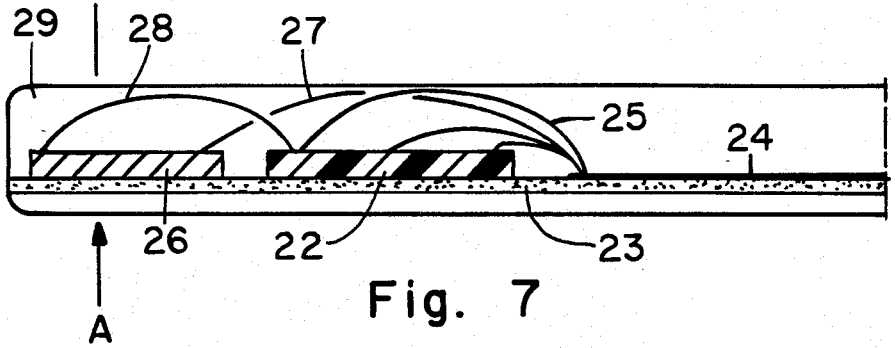
FIG. 7. shows the end elevation of device of FIG. 6.
Figure 8:
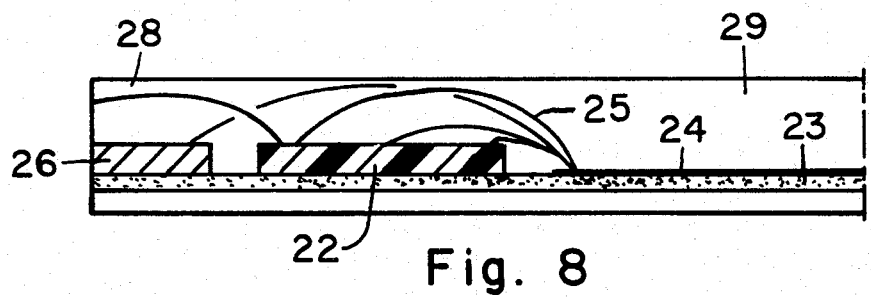
FIG. 8. shows the end elevation of device of FIG. 6 after completion of fabrication.
Figure 9:
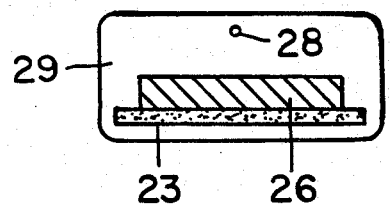
FIG. 9. shows the front elevation of device of FIG. 8.

I.C.A.S. fabrication I: TO-5 format (1) The integrated-circuit amplifier (FIG. 4) 12 is mounted onto a TO-5, or similar, microelectronic header 13. The chip is electrically connected to the header bonding posts 15 using well-known wire bonding techniques employing fine gauge (25 μm) gold wire 14.

(2) The header-chip wire bond to the inverting input of the amplifier is made 16 and the wire is not cut but pulled vertically upwards before being severed. (Alternatively, a separate bond to either the chip bonding pad or the header bonding post may be made and the wire drawn upwards as before). This provides a loose 25 μm diameter gold wire 17 bonded directly on, or indirectly to, the inverting input of the amplifier 12.

(3) A counter electrode (e.g. an anode) is formed by bonding another gold bonding wire on to an unused header post, in a similar fashion, or by using a larger diameter silver wire 18, electrically connected, and bonded to, a spare post.

Figure 5:
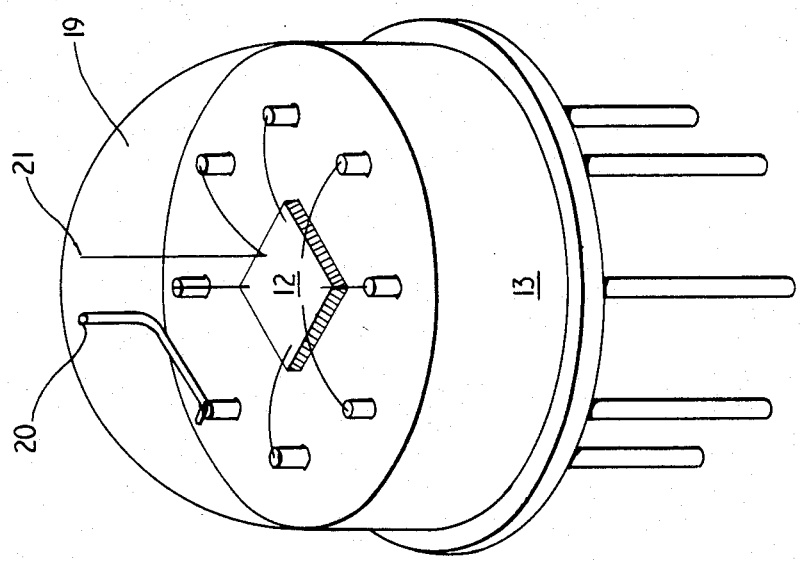
FIG. 5. shows a completed I.C.A.S. device (TO-5 form).

(4) An encapsulating agent is used to enclose all of the electrical connections on the surface of the header (FIG. 5). There are several agents suitable for this purpose. The general requirements are that the material must be a good electrical insulator, must be resistant to chemical attack, solvation and ionic penetration, must adhere well to the header surface, must have a viscosity low enough to flow around the delicate bonding wires without damaging them or the flying leadouts (17,18), and must be applicable using methods which are compatible with mass-fabrication processes. We have found that a slightly thixotropic epoxy is suitable, such as Epo-Tek H54 (Alpha Metals Ltd., Surrey, England), which may contain 1.8% Azo black dye as an optical mask (Alpha Metals Ltd.), but we have already described the use of a superior encapsulating agent, Bis-GMA (and Bis-GMA urethane adducts) in an earlier U.K. patent application (No. 8111199) for a similar purposes. Bis-GMA (an adduct for bis-phenol A and glyidyl metheracrylate [2,2-bis(p-(2-hydroxy 3-methacryloxy propoxy)phenyl)propane] is a photopolymerizable plastic used in the dental profession for sealing occlusal surfaces for the prevention of dental caries.

Several drops of Bis-GMA resin are applied to the surface of the header and flow over and around the bonding wires and the chip, forming a dome of fluid material 19. This is polymerized by brief (30-120 s) exposure to U.V. radiation, and the excess surface material is ultrasonically rinsed off (10 s) in isopropyl alcohol, or similar solvent.

(5) The sensing electrodes (20,21) are machined and polished flush with the surface of the encapsulating material.

I.C.A.S. fabrication II: catheter-tip format (1) The operational amplifier element 22 (FIGS. 6 to 9) is affixed with cyanoacrylate adhesive to the tip of a flexible printed circuit (FPC) strip comprising an array of copper strips 24 on a flexible plastic substrate 23 which is terminated with a suitable connector for electrical access. The amplifier is appropriately wire-bonded 25 to the conducting strips.

(2) A silver plate 26 approximately 1 mm×2 mm×0.2 mm is affixed to the tip of the FPC with cyanoacrylate adhesive.

(3) A wire bond 27 is formed between the proximal edge (i.e. chip side) of silver plate 26 and a conductive strip on the FPC.

(4) A gold wire bond 28 is made between the distal edge of silver plate 26 and the inverting input of the amplifier chip 22.

(5) The tip of the FPC is dip-coated in encapsulating material 29 (vide supra) which is polymerized as appropriate to the material.

(6) The tip of the assembly is machined away and polished, (FIG. 8), such that a gold bonding wire connected to the amplifier inverting input is exposed 28 and also disconnected from the silver plate 26 to which it was bonded for the purpose of simple fabrication.

(7) The assembly is mounted into a catheter-tip, if so required, for biomedical usage.

It must be noted that, in the descriptions hereinbefore, the terms "anode" and "cathode" are interchangeable, since, for the detection of oxygen, a positive polarizing voltage is required, whereas a negative polarizing potential is required for the detection of hydrogen peroxide in accordance with the electron reactions:

$$O_2 + 2H_2O + 2e^- \rightarrow H_2O + 2OH^- \qquad (1)$$

$$H_2O_2 + 2e^- \rightarrow 2OH^- \qquad (2)$$

The materials used for the anode and cathode may be selected according to the type of application required of the I.C.A.S. device, but the most common requirement is that the cathode (connected to amplifier inverting input) is gold, and that the anode is silver, subsequently electrolytically chloridised by well-known techniques to form a non-polarizable (i.e. reversible) silver/silver-chloride electrode. While we advocate a gold cathode and silver/silver-chloride anode, we do not rule out the use of other materials in this context, or of a remotely situated, i.e. non-integral, anode. For example, a stainless steel hypodermic needle has been used as the anode in a gold-cathode oxygen electrode (see "A hypodermic needle pO$_2$ electrode", Wahlen, W. J. and Spande, J. I., J. Appl. Physiol. (1980), 48, 186-7).

Figure 10:
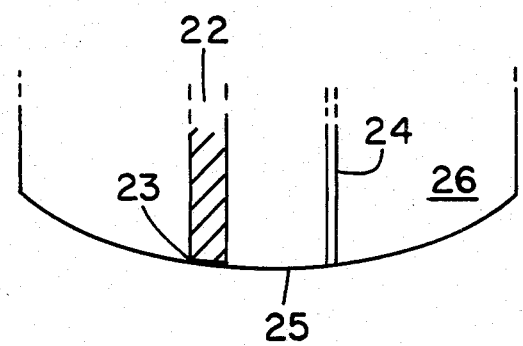
FIG. 10. shows an I.C.A.S. electrode tip with bare electrodes.
Figure 11:
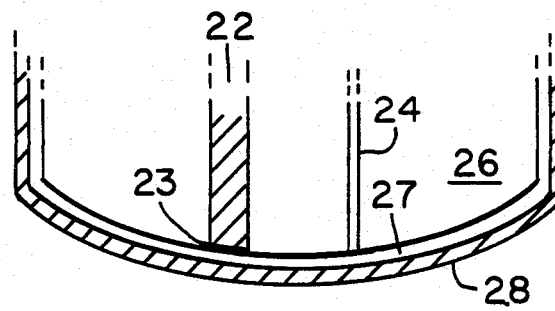
FIG. 11. shows an I.C.A.S. electrode tip with additional films or membranes deposited over the bare electrodes.

The active, chemical-sensing surface of the I.C.A.S. device is shown in simplified form in FIG. 10, and comprises typically a silver anode 22 with chloridised, exposed tip 23 and a gold cathode 24 contained in chemically-resistant encapsulation 26. The use of bare electrodes of this type in blood analysis may sometimes initiate protein deposition on the electrode surfaces. FIG. 11 shows an improved system for biomedical application incorporating a thin film of phosphate buffer in agarose gel form 27 and a gas permeable membrane 28 affixed to the device surface by dip-coating, or other means, so that the electrode system is partitioned from the blood sample under test. The membrane may be made from polypropylene, polyethylene, teflon or similar material such as is used in conventional electrode systems, and having a typical thickness of 20 μm.

Figure 12:
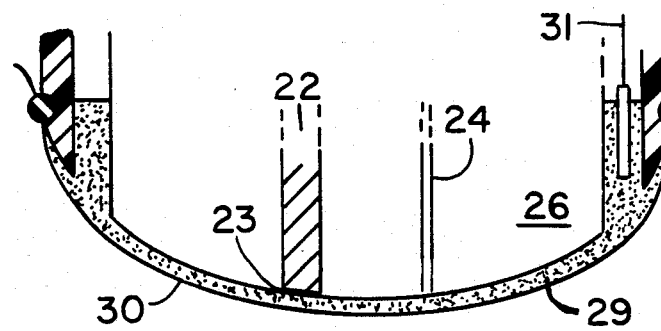
FIG. 12. shows an I.C.A.S. engineered into a conventional $pO_2$ measurement cell.

I.C.A.S. devices may be used in conventional electrode assemblies to act as superior replacements for the active conventional elements (e.g. platinum in glass) as shown in FIG. 12, where a device, as described in FIG. 10, is mounted into a holster 32 containing a phosphate buffer 29 and having a gas-permeable membrane 30 located over the I.C.A.S. with a rubber or silastic O-ring 33. A remote silver/silver-chloride anode 31 may be used if already present in a conventional electrode holster.

Figure 13:
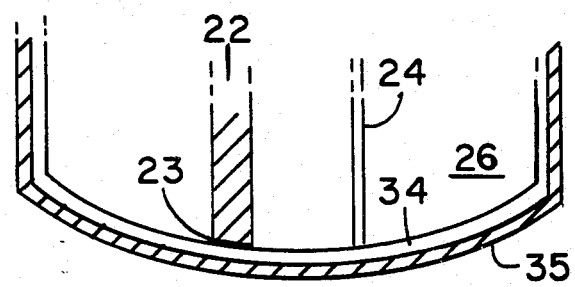
FIG. 13. shows an I.C.A.S. device engineered as an enzyme-responsive electrode.

A further important application of I.C.A.S. devices is their use as enzymatic-responsive sensors, when appropriately modified (FIG. 13). This involves the attachment of one or more suitable membranes 34,35 to the surface of a bare I.C.A.S., by dip-coating, physically locating or other means, and polarizing the secondary electrode (i.e. not the electrode connected directly to the integral amplifier) at approximately −650 mV such that the device acts as a hydrogen peroxide sensor and generates a signal in proportion to the amount of hydrogen peroxide oxidised at the primary electrode. The membrane or membranes may be polymer coatings of immobilized enzyme, such that an enzymatic reaction, with or without appropriate co-factors, which liberates hydrogen peroxide:

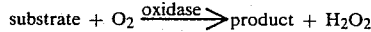

can be sensed by the I.C.A.S. device. Typically, glucose oxidase can be used for glucose, and lactate dehydrogenase for lactate. Modifications of this type with respect to conventional amperometric electrodes have already been referred to (Bertrand et al., supra).

Figure 14:
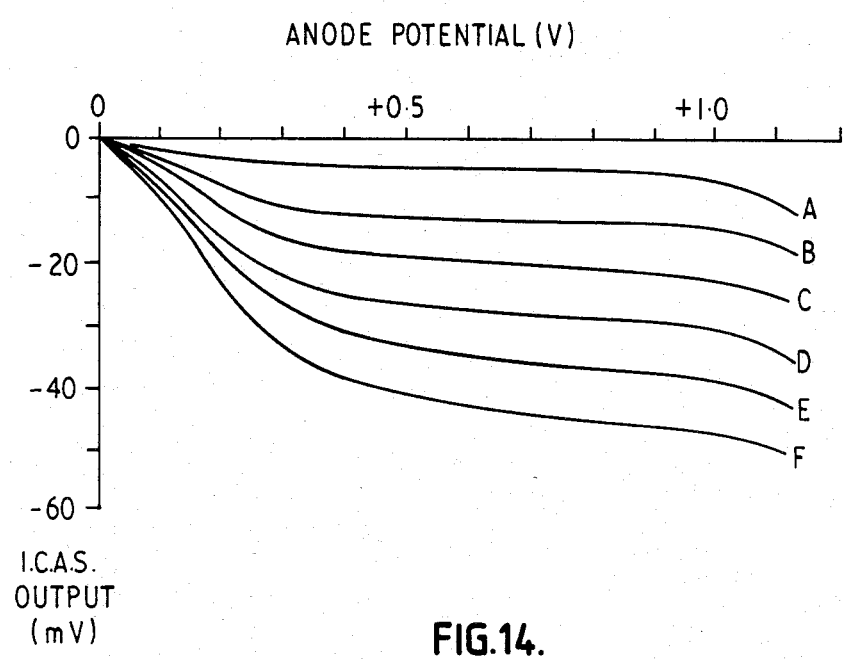
FIG. 14. shows an response characteristics of an I.C.A.S. device (TO-5 type).

FIG. 14 shows the response characteristics of an I.C.A.S. fabricated according to the methods described above (I.C.A.S. fabrication I: TO-5 format), using Bis-GMA encapsulant polymerized with U.V. light for 120 seconds, and employing a CA 3140 amplifier with 10 megohm element feedback resistor, a 25 μm diameter Au-1% Si bond-wire cathode, and a 0.7 mm×0.3 mm silver anode, surface-chloridised in 0.1 mol dm$^{-3}$ HCl at 50 μA for 5 seconds.

The device was amounted on the tip of a polycarbonate tube, forming a dip-type sensor, and supported in 25 ml 0.2 mol dm$^{-3}$ KCl solution at 24° C. An oxygen/nitrogen gas stream was bubbled through the solution from a Wösthoff pumping system, set initially to deliver 0% O$_2$; 100% N$_2$, and a current-voltage curve was obtained (FIG. 14, curve A) by sweeping the anode potential from 0 V to +1.1 V in 10 mV increments (2 s/increment) under minicomputer control (HP 9815). The oxygen percentage in the gas mixture was incremented by 10% and after the system had equilibrated, a second current-voltage curve was obtained (FIG. 14, curve B). This process was repeated up to a 50% oxygen level (FIG. 14, curve F), allowing a set of curves to be obtained.

We claim:

1. A miniature sensor assembly for the detection and electrochemical measurement of oxygen and other chemical properties of the environment to which it is exposed, said sensor comprising:
   an electrically insulating substrate comprising a microelectronic header having a first surface,
   an integrated circuit amplifier mounted on said first surface of said substrate, said amplifier having at least an input terminal,
   a plurality of conductive posts situated around the periphery of said first surface of said substrate, said amplifier being centrally disposed with respect to said posts,
   said amplifier, said plurality of conductive posts, and the adjacent surface of said substrate being encapsulated in a chemically-resistant, electrically inert material having at least one exposed surface,
   a first noble metal wire connected at one end thereof to one of said conductive posts, said noble metal wire being connected at a point between the ends thereof to said amplifier input terminal, the end of said first noble metal wire opposite said one end extending from said amplifier input terminal in a direction substantially perpendicular to the first surface of said header and terminating at said exposed surface of said electrically inert material, and
   a conductive electrode encapsulated in said electrically inert material, one end of said conductive electrode terminating at said exposed surface of said electrically inert material, said conductive electrode being electrically connected to one of said plurality of conductive posts, said electrically inert material surrounding said first noble metal wire and said conductive electrode throughout their entire lengths.

2. A sensor in accordance with claim 1 wherein said conductive electrode comprises a second noble metal wire connected at one end to one of said conductive posts, at least a portion of the remaining end of second noble metal wire extending in a direction substantially perpendicular to the first surface of said substrate.

3. A sensor in accordance with claim 2 wherein said first and second noble metal wires are formed of gold.

4. A sensor in accordance with claim 2 wherein said first noble metal wire is formed of gold and said second noble metal wire is formed of silver, the diameter of said second noble metal wire being larger than that of said first noble metal wire.

5. A sensor in accordance with claim 2 further comprising a film containing an electrolyte disposed over at least a portion of said exposed surface of said electrically inert material and covering the exposed end of at least one of said first noble metal wire and said conductive electrode, and a thin gas-permeable membrane disposed over the surface of said film.

* * * * *